(12) United States Patent
Nishio et al.

(10) Patent No.: US 10,821,301 B2
(45) Date of Patent: Nov. 3, 2020

(54) TREATMENT ASSISTANCE SYSTEM AND OPERATION METHOD THEREFOR, AND STORAGE MEDIUM FOR STORING TREATMENT ASSISTANCE PROGRAM

(71) Applicants: MIZUHO INFORMATION & RESEARCH INSTITUTE, INC., Tokyo (JP); NATIONAL UNIVERSITY CORPORATION HIROSHIMA UNIVERSITY, Hiroshima (JP)

(72) Inventors: Teiji Nishio, Hiroshima (JP); Akito Saito, Hiroshima (JP); Yasushi Nagata, Hiroshima (JP); Makiko Suitani, Tokyo (JP); Daiki Hashimoto, Tokyo (JP); Takeshi Nagata, Tokyo (JP); Hidemasa Maekawa, Tokyo (JP)

(73) Assignees: MIZUHO INFORMATION & RESEARCH INSTITUTE, INC., Tokyo (JP); NATIONAL UNIVERSITY CORP HIROSHIMA UNIVERSITY, Hiroshima (JP)

(*) Notice: Subject to any disclaimer, the term of this patent is extended or adjusted under 35 U.S.C. 154(b) by 384 days.

(21) Appl. No.: 15/765,983

(22) PCT Filed: Nov. 2, 2016

(86) PCT No.: PCT/JP2016/082528
§ 371 (c)(1),
(2) Date: Apr. 4, 2018

(87) PCT Pub. No.: WO2017/086154
PCT Pub. Date: May 26, 2017

(65) Prior Publication Data
US 2019/0308033 A1    Oct. 10, 2019

(30) Foreign Application Priority Data

Nov. 18, 2015 (JP) ................................ 2015-226023

(51) Int. Cl.
*A61N 5/10* (2006.01)
*A61B 6/03* (2006.01)
*A61B 6/00* (2006.01)

(52) U.S. Cl.
CPC ............ *A61N 5/1039* (2013.01); *A61B 6/032* (2013.01); *A61B 6/5247* (2013.01); *A61N 5/10* (2013.01);
(Continued)

(58) Field of Classification Search
CPC .................. A61B 6/032; A61B 6/5247; A61N 2005/1061; A61N 5/10; A61N 5/1039; A61N 5/1049
See application file for complete search history.

(56) References Cited

U.S. PATENT DOCUMENTS

2003/0112922 A1   6/2003   Burdette et al.
2007/0189455 A1   8/2007   Allison
(Continued)

FOREIGN PATENT DOCUMENTS

JP   2008022896 A   2/2008
JP   2009526620 A   7/2009
(Continued)

OTHER PUBLICATIONS

International Preliminary Report on Patentability for PCT/JP2016/082528 dated May 22, 2018, 7 pages.
(Continued)

*Primary Examiner* — Mark D Remaly
(74) *Attorney, Agent, or Firm* — Kilpatrick Townsend & Stockton LLP (57) ABSTRACT

A system that assists in treatment includes circuitry configured to generate three-dimensional body data of a patient using data obtained from a three-dimensional measurement unit, obtain a tomographic image of the patient from a body tomographic measurement apparatus, execute an examination assist process, which aligns the three-dimensional body data with the tomographic image, execute a treatment plan (Continued)

assist process, which make a treatment plan that specifies a posture of the patient when treatment is performed using the tomographic image and the three-dimensional body data that are aligned with each other, and execute a treatment assist process, which outputs a treatment instruction based on the posture specified in the treatment plan.

7 Claims, 6 Drawing Sheets

(52) U.S. Cl.
CPC .... *A61N 5/1049* (2013.01); *A61N 2005/1061* (2013.01)

(56) References Cited

U.S. PATENT DOCUMENTS

2010/0246915 A1   9/2010   Yamakoshi et al.
2011/0107270 A1   5/2011   Wang et al.
2013/0090547 A1   4/2013   Bani-Hashemi
2014/0049629 A1*  2/2014   Siewerdsen ............ A61B 34/20
                                                348/77

FOREIGN PATENT DOCUMENTS

| JP | 2012254243 A | 12/2012 |
| JP | 2015205110 A | 11/2015 |
| JP | 2017035343 A | 2/2017 |

OTHER PUBLICATIONS

Extended European Search Report for EP 16 86 6156 completed Apr. 10, 2019, 7 pages.
International Search Report corresponding to PCT/JP2016/082528, dated Nov. 2, 2016, two pages.

* cited by examiner

TREATMENT ASSISTANCE SYSTEM AND OPERATION METHOD THEREFOR, AND STORAGE MEDIUM FOR STORING TREATMENT ASSISTANCE PROGRAM

TECHNICAL FIELD

The present invention relates to a treatment assist system assisting in treatment that uses, for example, radiation, a method for operating the treatment assist system, and a storage medium that stores a treatment assist program.

BACKGROUND ART

A treatment apparatus that uses radiation such as X-rays, gamma rays, or particle beams of protons or heavy ions has been proposed for a purpose of cancer treatment. Such a treatment apparatus needs to intensively irradiate an affected part, while not affecting normal cells. In this case, irradiation of the affected part such as cancer with high accuracy is important in radiation treatment and particle therapy. Hence, a technique for positioning a radiation treatment patient has been proposed (for example, refer to patent document 1). The technique described in this document collates a three-dimensional reference image with a present three-dimensional image and calculates a body position correction amount so that the position and orientation of an affected part in the present image matches the position and orientation of the affected part in the reference image. More specifically, a primary collation is performed on the present image with reference to the reference image. Additionally, a predetermined template region is formed from one of the reference image and the present image based on the result of the primary collation, and a predetermined search subject region is formed from the other one of the reference image and the present image, which differs from the base for forming the predetermined template region, based on the result of the primary collation. A secondary collation is performed on the predetermined search subject region with reference to the predetermined template region.

Additionally, a positioning device that performs a high accuracy positioning in a shorter time has been proposed (for example, refer to patent document 2). The technique described in patent document 2 measures the body surface of a patient through a three-dimensional measurement technique that uses measurement light and a camera. Then, body surface reference position data, which is obtained in advance, is compared and collated with body surface measurement position data, which is obtained during treatment or an examination by a three-dimensional optical measuring means, to obtain a position orientation conversion parameter. The position orientation conversion parameter is used to adjust the position and angle of a support table for the patient so that the difference between the body surface reference position data and the body surface measurement position data is set in a tolerance range.

PRIOR ART DOCUMENT

Patent Document

Patent Document 1: Japanese Laid-Open Patent Publication No. 2012-254243

Patent Document 2: Japanese Laid-Open Patent Publication No. 2008-22896

SUMMARY OF THE INVENTION

Problems that are to be Solved by the Invention

However, with the technique described in patent document 1, images are captured multiple times. In this case, the multiple radiation irradiations increase the load on the patient. With the technique described in patent document 2, the posture can be reproduced during an examination and treatment. However, it is difficult to make a treatment plan that takes account of the affected region based on only the reproduction of the patient posture. Additionally, when the body of the patient is moved closer to an irradiation device to increase the irradiation efficiency during treatment, the body (e.g., arm) of the patient may come into contact with the irradiation device.

It is an object of the present invention to provide a system assisting in an accurate treatment that uses, for example, radiation while reducing the load on the patient, a method for operating the system, and a storage medium that stores a program for the system.

Means for Solving the Problem

To achieve the above object, one aspect provides a system that assists in treatment. The system includes a control section configured to generate three-dimensional body data of a patient using data obtained from a three-dimensional measurement unit, obtain a tomographic image of the patient from a body tomographic measurement apparatus, execute an examination assist process, which aligns the three-dimensional body data with the tomographic image, execute a treatment plan assist process, which make a treatment plan that specifies a posture of the patient when treatment is performed using the tomographic image and the three-dimensional body data that are aligned with each other, and execute a treatment assist process, which outputs a treatment instruction based on the posture specified in the treatment plan. Thus, an accurate treatment plan is made using the three-dimensional body data of the patient in addition to the tomographic image. Accordingly, the above aspect assists in an accurate treatment using, for example, radiation while reducing the load on the patient.

Preferably, in the above treatment assist system, the control section is configured to generate body contour data in a format that is the same as the tomographic image based on the three-dimensional body data, generate image data in which the body contour data is combined with the tomographic image, and execute the treatment plan assist process using the combined image data. Thus, a treatment plan for performing an efficient treatment is made taking account of the body shape in the same format.

Preferably, in the above treatment assist system, in the treatment assist process, the control section is configured to reobtain three-dimensional body data of the patient, compare the reobtained three-dimensional body data with three-dimensional body data of the posture specified in the treatment plan, and output a treatment instruction including a result of the comparison. Thus, the treatment is performed based on the posture formed during the treatment planning.

Preferably, in the above treatment assist system, in the examination assist process, the control section is configured to align the three-dimensional body data with the tomographic image based on a feature point included in the three-dimensional body data and a feature point included in the tomographic image. Thus, the three-dimensional body data is aligned with the tomographic image using the feature points of, for example, the body shape.

In the above treatment assist system, when capturing a tomographic image, the body tomographic measurement apparatus is configured to irradiate the patient with reference light that specifies a coordinate of the tomographic image. When generating three-dimensional body data, the three-dimensional measurement unit is configured to capture an image of the patient including a position irradiated with the reference light. The control section is configured to align the three-dimensional body data with the tomographic image based on the position irradiated with the reference light. Thus, the three-dimensional body data is aligned with the tomographic image using the reference light.

Preferably, in the above treatment assist system, the control section is configured to prompt an operator to recapture a tomographic image based on the result of the comparison. Thus, a re-examination may be prompted when the body shape has been significantly changed.

To achieve the above object, another aspect provides a method for operating a system that assists in treatment. The method includes generating three-dimensional body data of a patient using data that is obtained from a three-dimensional measurement unit with a control section, obtaining a tomographic image of the patient from a body tomographic measurement apparatus with the control section, aligning the three-dimensional body data with the tomographic image with the control section, making a treatment plan that specifies a posture of the patient when treatment is performed with the control section using the tomographic image and the three-dimensional body data that are aligned with each other, and outputting a treatment instruction with the control section based on the posture specified in the treatment plan.

To achieve the above object, a further aspect provides a non-transitory computer readable storage medium including a program that assists in treatment with a treatment assist system. The program instructs the treatment assist system to execute generating three-dimensional body data of a patient using data obtained from a three-dimensional measurement unit, obtaining a tomographic image of the patient from a body tomographic measurement apparatus, aligning the three-dimensional body data with the tomographic image, making a treatment plan that specifies a posture of the patient when treatment is performed using the tomographic image and the three-dimensional body data that are aligned with each other, and outputting a treatment instruction based on the posture specified in the treatment plan.

EMBODIMENTS OF THE INVENTION

One embodiment of the present invention will now be described with reference to FIGS. 1 to 6. In the present embodiment, it is assumed that treatment is performed on a patient having an affected part inside the body by irradiating the affected part with radiation. In this specification, if appropriate, the term "doctor" includes any other medical professionals who participate in, assist in, or perform at least one of diagnosis and treatment such as a clinical radiologist and a nurse.

Figure 1:
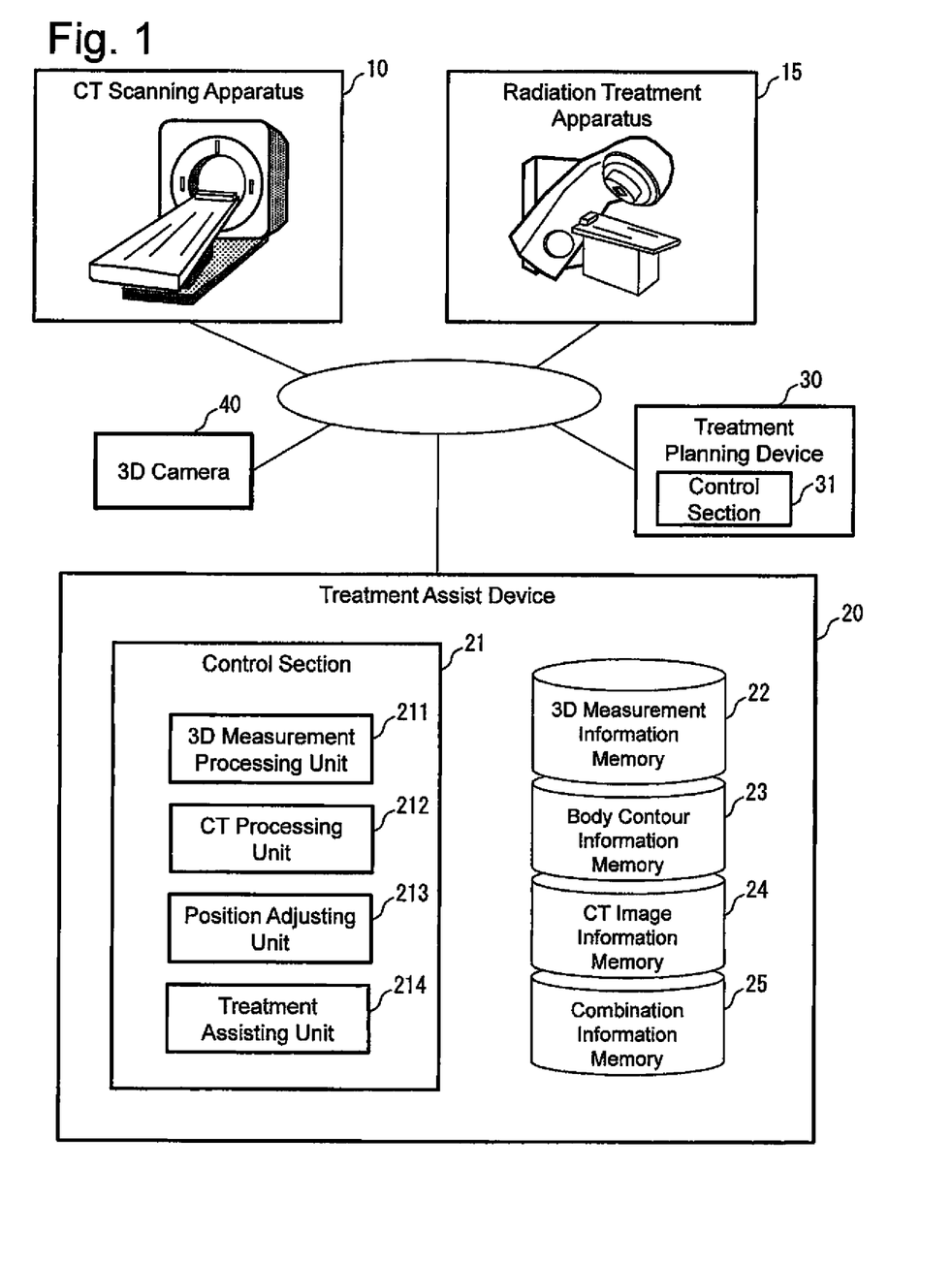
FIG. 1 is a schematic diagram showing a present embodiment of a system.

As shown in FIG. 1, to assist in a treatment that uses, for example, radiation such as that described above, a treatment assist system includes a CT scanning apparatus 10, a radiation treatment apparatus 15, a treatment assist device 20, a treatment planning device 30, and a 3D camera 40.

The CT scanning apparatus 10 functions as a body tomographic measurement apparatus to perform a computed tomography (CT) process, which scans an object using radiation or the like and produces an internal image (CT image data) of the body processed by a computer. The computed tomography stores a plurality of CT images obtained by capturing images of the body of a patient at predetermined image intervals. The CT images are stored in a medical image format (DICOM: Digital Imaging and Communication in Medicine).

The radiation treatment apparatus 15 performs treatment for, for example, cancer by irradiating an affected part with radiation. The radiation treatment apparatus 15 includes an irradiation device (gantry), which emits irradiation, and a treatment table, on which a patient lies in a supine position or a prone position.

The treatment planning device 30 is a simulator that studies a means for striking radiation on the affected part to determine whether an appropriate amount of radiation is provided. The treatment planning device 30 obtains the CT images (DICOM data), which are captured at predetermined image intervals, from the CT scanning apparatus 10. Then, the treatment planning device 30 performs a contour extraction on the DICOM data using a known method to generate CT contour information. The CT contour information, which includes DICOM ROI (Region Of Interest) data, is data including aggregation of points (coordinates) defining contours of predetermined portions (body surface, bone, affected part, at-risk organ, etc.) specified in the CT images (tomographic images) captured at the predetermined intervals.

The treatment planning device 30 is configured to determine, for example, a radiation quality of treatment beams, an incident direction, an irradiation range, a radiation amount, and the number of times irradiations are performed, based on the body surface shape of an affected part, the shape of the affected part, the position, and the positional relationship with an at-risk organ. The treatment planning device 30 includes a control section 31, which includes a computer or the like, an input portion such as a keyboard or a pointing device used by a doctor, and an output portion such as a display. The control section 31 of the treatment planning device 30 is configured to execute a treatment plan assist process when the treatment assist system executes a treatment assist program.

The 3D camera 40, which functions as a three-dimensional measurement unit, includes, for example, an RGB image capturing unit, a motion sensor, and a depth sensor. The 3D camera 40 is capable of recognizing the position and motion of a subject. The 3D camera 40 outputs a captured image of the subject. The captured image includes, for each subject included in the field of view, a view point movement and a view direction, which are measured by the motion sensor, and distance information (depth information), which is measured by the depth sensor. This allows for reconstruction of a three-dimensional model taking account of the positions where a plurality of images is captured.

The treatment assist device 20 is a computer system that assists in radiation treatment for a patient. The treatment assist device 20 includes a control section 21, a three-dimensional measurement information memory 22, a body contour information memory 23, a CT image information memory 24, and a combination information memory 25. The treatment assist device 20 further includes an input portion such as a keyboard or a pointing device operated by a doctor and an output portion such as a display.

The control section 31 of the treatment planning device 30 and the control section 21 of the treatment assist device 20 may each be realized by, for example, circuitry, that is, one or more dedicated hardware circuits such as ASICs, one or more processing circuits that operate in accordance with a computer program (software), or the combination of these. The processing circuits include a CPU and a memory (e.g., ROM and RAM) that stores programs executed by the CPU. The memory, or a computer readable storage medium, includes any applicable medium that is accessible by a versatile or dedicated computer.

The control section 21, which functions as a controlling means that includes, for example, a CPU, a RAM, and a ROM, executes processes (processes including, for example, three-dimensional measurement processing step, CT processing step, position adjusting step, treatment assisting step) that will be described later. When the treatment assist system executes the treatment assist program, the control section 21 functions as, for example, a three-dimensional measurement processing unit 211, a CT processing unit 212, a position adjusting unit 213, and a treatment assisting unit 214. The processes executed by the control section 21 include an examination assist process and a treatment assist process.

The three-dimensional measurement processing unit 211 executes a process for obtaining captured images from the 3D camera 40. Additionally, the three-dimensional measurement processing unit 211 executes a process for reconstructing the obtained captured images to form a three-dimensional model (mesh model) of the body of the patient. The three-dimensional measurement processing unit 211 also executes a process for forming body contour data, which will be described later, from the three-dimensional model. Thus, the three-dimensional measurement processing unit 211 holds data related to contour formation intervals, which are used to generate the body contour data from the three-dimensional model. In the present embodiment, the contour formation intervals and intervals at which CT images are captured use the same distances.

The CT processing unit 212 executes a process for obtaining CT images from the treatment planning device 30.

The position adjusting unit 213 executes a process for aligning the CT contour information, which is generated from the CT images, with the three-dimensional model, which is formed from the images captured by the 3D camera 40.

The treatment assisting unit 214 executes a process for assisting in alignment such as the posture of the patient. The treatment assisting unit 214 holds data related to a misalignment amount, which determines the reproduction of the posture, and data related to a deformation reference value, which determines a change in the body shape of the patient.

Figure 2A:
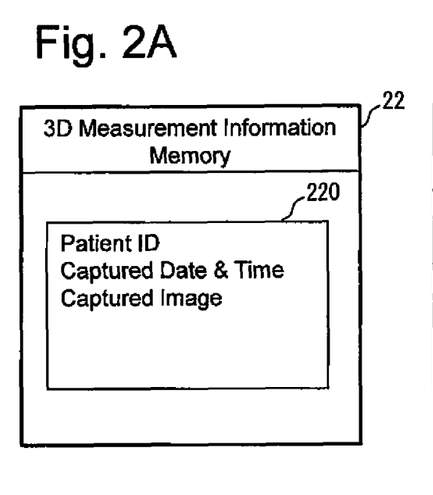
FIG. 2A is a diagram of data stored in a three-dimensional measurement information memory of the system of FIG. 1.

As shown in FIG. 2A, the three-dimensional measurement information memory 22 stores three-dimensional measurement data 220 of captured images of a patient subject to treatment by the 3D camera 40. The three-dimensional measurement data 220 is stored when the captured images are obtained from the 3D camera 40 during an examination (CT scanning). The three-dimensional measurement data 220 includes the patient ID, the captured date and time, and data related to the captured images.

A patient ID data region stores data related to an identifier that identifies the patient.

A captured date and time data region stores data related to the year, month, day, and time at which the examination (CT scan) is performed.

A captured image data region stores data related to the captured images obtained from the 3D camera 40. The captured images embed data related to a view point movement corresponding to movement of the 3D camera 40, a view direction, and a distance (depth) to the subject. In the present embodiment, the captured images are used to form a three-dimensional model (three-dimensional body data) related to the body shape of the patient.

Figure 2B:
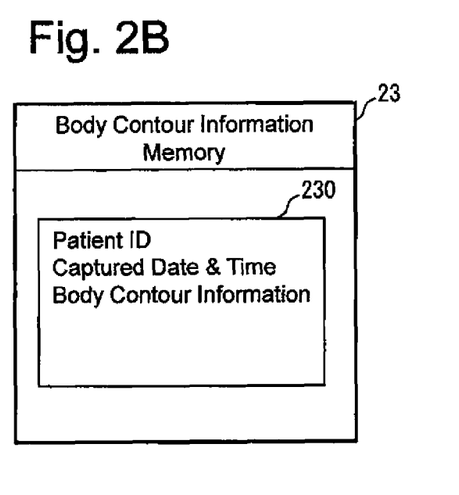
FIG. 2B is a diagram of data stored in a body contour information memory of the system of FIG. 1.

As shown in FIG. 2B, the body contour information memory 23 stores body contour control data 230 of the three-dimensional model, which is formed by the captured images of the patient. The body contour control data 230 is stored when a three-dimensional model is reconstructed using the captured images. The body contour control data 230 includes the patient ID, the captured date and time, and data related to the body contour information.

A patient ID data region stores data related to the identifier that identifies the patient.

A captured date and time data region stores data related to the year, month, day, and time at which the CT images are captured.

A body contour information data region stores data related to the body contour that is formed based on the three-dimensional model obtained from the 3D camera 40. The body contour data includes the contours of tomographies of the three-dimensional model corresponding to tomographic intervals at which the CT images are captured through CT scanning. In the present embodiment, in the same manner as the contour extraction result of the CT images, the body contour data uses the DICOM ROI format.

Figure 2C:
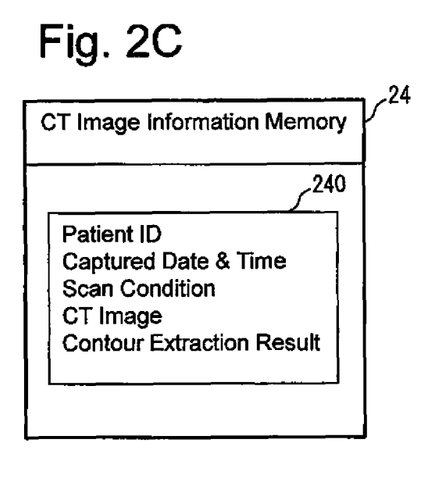
FIG. 2C is a diagram of data stored in a CT image information memory of the system of FIG. 1.

As shown in FIG. 2C, the CT image information memory 24 stores CT image data 240 related to a tomographic structure of the patient body. The CT image data 240 is stored when CT images are captured by the CT scanning apparatus 10 and the CT images and the contour information are obtained from the treatment planning device 30. The CT image data 240 include the patient ID, the captured date and time, the scan condition, the CT images, and data related to the contour extraction result.

A patient ID data region stores data related to the identifier that identifies the patient.

A captured date and time data region stores data related to the year, month, day, and time at which the CT images are captured.

A scan condition data region stores data related to a condition (e.g., image interval) under which the CT images are captured.

A CT image data region stores the CT images (tomographic images) that are captured by the CT scanning apparatus 10.

A contour extraction result data region stores contour information (DICOM ROI data) extracted from the CT images. The contour information indicates positions of contours of a predetermined portion (body surface, bone, affected part, at-risk organ, etc.) contained in the CT images. The contour information is used to specify the shape (CT body surface shape) of the body surface indicated at image intervals of the CT images (tomographic images).

Figure 2D:
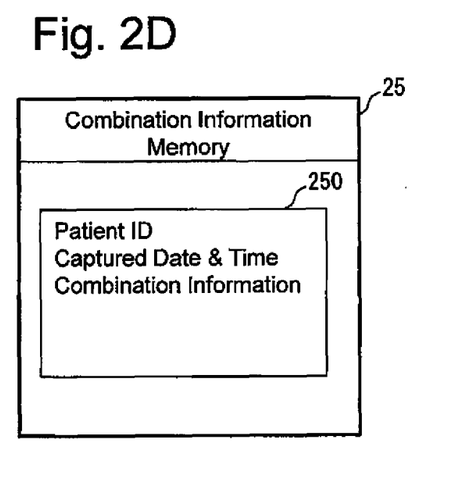
FIG. 2D is a diagram of data stored in a combination information memory of the system of FIG. 1.

As shown in FIG. 2D, the combination information memory 25 stores combination control data 250, in which the body contour data formed using the capture images has been aligned with the CT body surface shape formed using the CT images. The combination control data 250 is stored when the alignment is performed on the three-dimensional model. The combination control data 250 includes the patient ID, the captured date and time, and data related to the combination information.

A patient ID data region stores data related to the identifier that identifies the patient.

A captured date and time data region stores data related to the year, month, day, and time at which the CT images of the patient are captured.

A combination information data region stores combination data in which the CT images are combined with the body contour data based on the alignment of the CT body surface shape with the three-dimensional model. In the present embodiment, the combination data uses the DICOM ROI format.

The procedures for performing the method for operating the treatment assist system, which includes the treatment assist device 20 having the above configuration, will now be described with reference to FIGS. 3 to 6.

Process Schema

Figure 3:
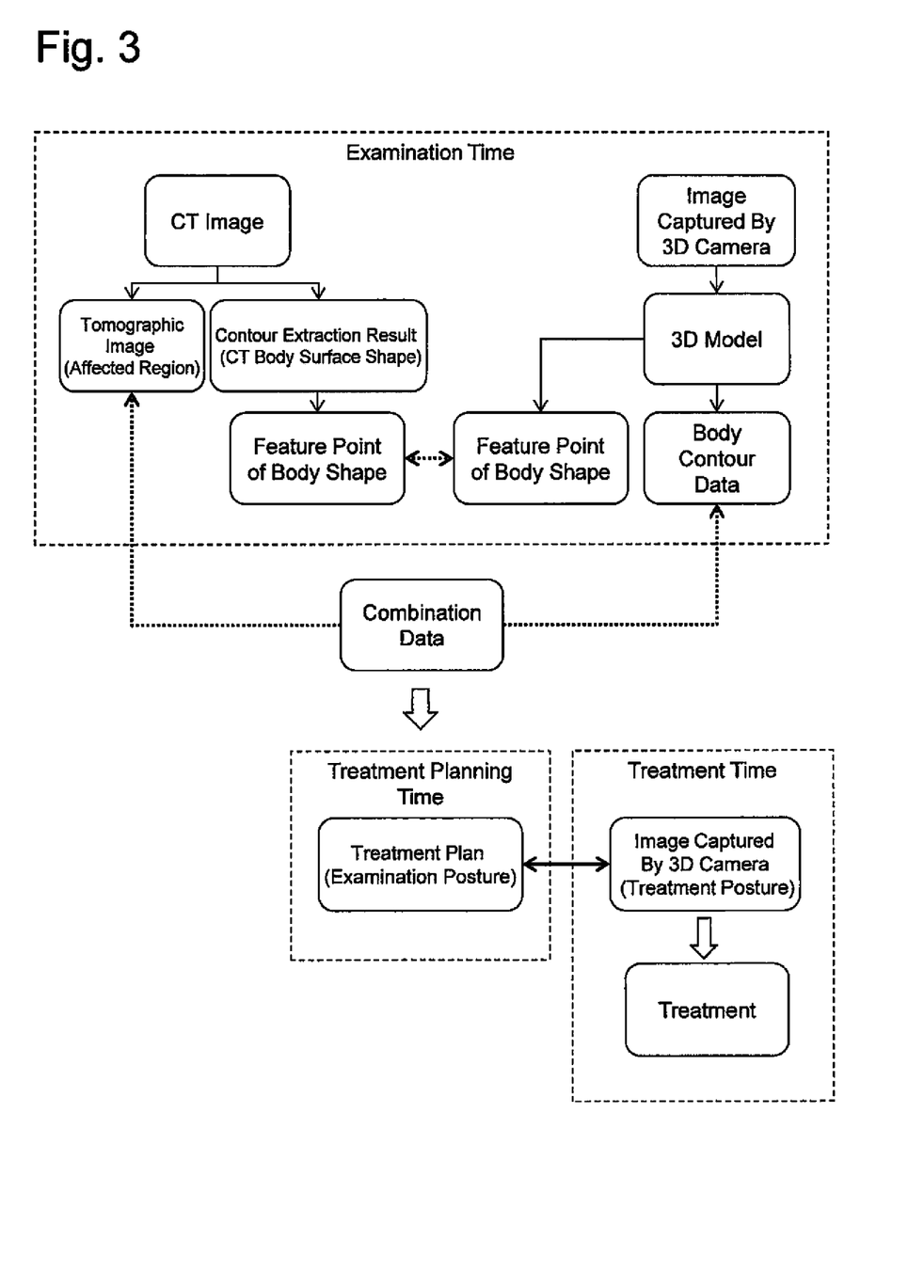
FIG. 3 is a schematic diagram of processes in the system of FIG. 1.

The schema of processes performed by the treatment assist system of the present embodiment will now be described with reference to FIG. 3.

During an examination, CT images (DICOM data), which are captured by the CT scanning apparatus 10, and a contour extraction result (DICOM ROI data) are obtained. Then, feature points of the body shape are specified based on the contour extraction result. Additionally, an affected region is specified based on the CT images and the contour extraction result of the CT images.

Additionally, during the examination, when CT scanning is performed on a patient, images of the patient captured by the 3D camera 40 are obtained. The captured images are used to form a three-dimensional model. Then, feature points of the body shape are specified in the three-dimensional model. The feature points obtained based on the contour extraction result of the CT images are compared with the feature points of the three-dimensional model to align the CT images with the three-dimensional model. This alignment generates combination data in which the CT images are combined with the body contour data generated from the three-dimensional model.

Figure 4A:
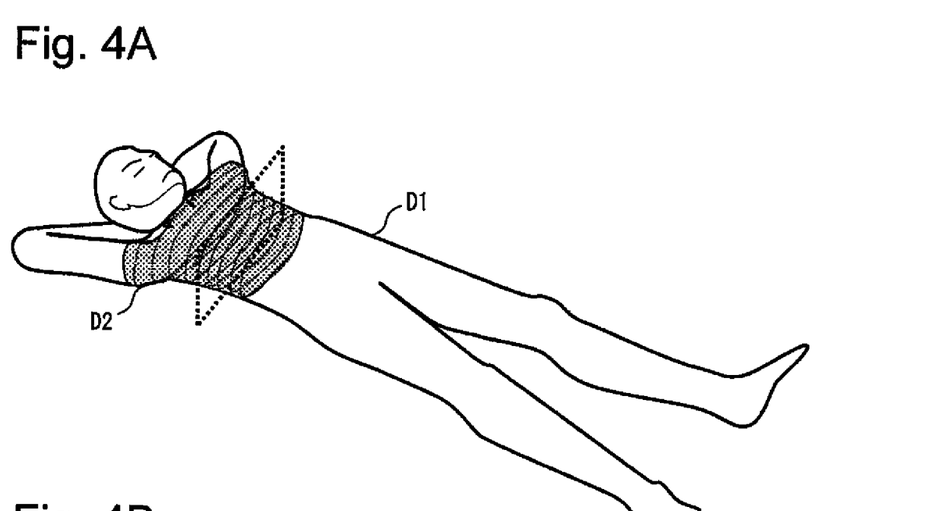
FIG. 4A is a diagram of an alignment process in the system of FIG. 1 showing the positional relationship between a three-dimensional model captured by a 3D camera and a CT scan region.
Figure 4B:
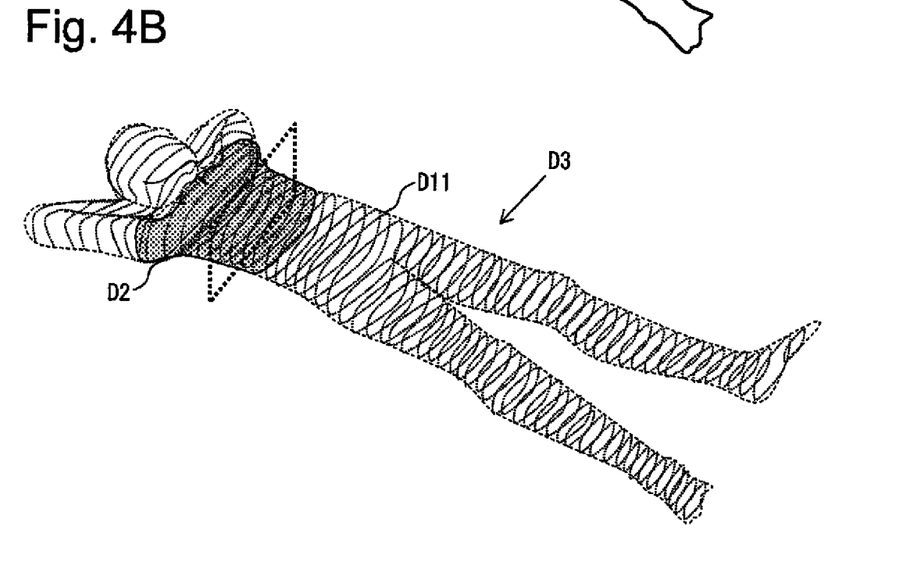
FIG. 4B is a diagram of the alignment process in the system of FIG. 1 showing the positional relationship between body contour data, which is generated from the three-dimensional model, and the CT scan region.

As shown in FIG. 4A, a three-dimensional model D1, which is imaged by the 3D camera 40, is aligned with a contour extraction result D2 of the CT images. Then, as shown in FIG. 4B, body contour data D11, which includes contours of tomographies extracted from the three-dimensional model D1, is generated. The body contour data D11 is aligned with the contour extraction result D2 of the CT images and the CT images. Thus, combination data D3 may be used to recognize the shape of a body region where the CT scanning is not performed based on the same data format (DICOM ROI data).

When making a treatment plan, a simulation that uses the generated combination data is performed to make a treatment plan in which the irradiation position, the irradiation direction, and the irradiation amount are calculated for when the affected region of the CT images is irradiated with radiation.

During the treatment, the posture of the patient in the radiation treatment apparatus 15 is compared with the posture of the patient used in the treatment plan. Under a condition in which the postures conform to each other, the radiation treatment apparatus 15 performs the treatment based on the treatment plan.

Examination Assist Process

Figure 5A:
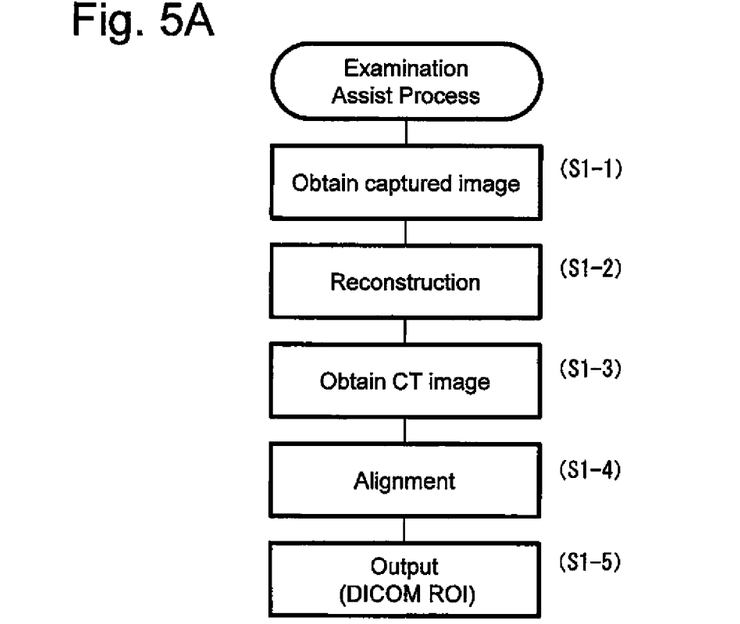
FIG. 5A is a chart showing the procedures for performing an examination assist process in the system of FIG. 1.

The examination assist process will now be described with reference to FIG. 5A.

The control section 21 of the treatment assist device 20 executes a process for obtaining captured images (step S1-1). More specifically, images of the posture of a patient on the treatment table of the CT scanning apparatus 10 (examination posture) are captured by the 3D camera 40. At this time, the treatment table of the CT scanning apparatus 10 is also included in the image. The three-dimensional measurement processing unit 211 of the control section 21 obtains the captured data from the 3D camera 40 together with the patient ID. The captured data includes data related to the captured images including the view point movement from a predetermined original point, the view direction, and information of a depth to the subject (e.g., each pixel). The three-dimensional measurement processing unit 211 stores the three-dimensional measurement data 220, which includes the captured images associated with the patient ID and the captured date and time, in the three-dimensional measurement information memory 22.

The control section 21 of the treatment assist device 20 executes a reconstruction process (step S1-2). More specifically, the three-dimensional measurement processing unit 211 of the control section 21 forms a three-dimensional model by reconstructing the captured images of the three-dimensional measurement data 220, which is stored in the three-dimensional measurement information memory 22, in a virtual space using the view point movement, the view direction, and the depth direction. The three-dimensional measurement processing unit 211 specifies contours of tomographies corresponding to the contour formation intervals (tomographic intervals at which CT images are captured) in the three-dimensional model to generate body contour data for the patient. The body contour data uses the DICOM ROI format. The three-dimensional measurement processing unit 211 stores the body contour data in the body contour information memory 23 associating with the patient ID and the captured date and time.

The control section 21 of the treatment assist device 20 executes a process for obtaining CT images (step S1-3). More specifically, the CT scanning apparatus 10 performs a computed tomography process on a specified region of the patient to form CT images (DICOM data). The treatment planning device 30 extracts contours using the CT images to produce a contour extraction result (DICOM ROI data). The CT processing unit 212 of the treatment assist device 20 stores the CT images and the contour extraction result, which are obtained from the treatment planning device 30, in the CT image information memory 24.

The control section 21 of the treatment assist device 20 executes an alignment process (step S1-4). More specifically, the position adjusting unit 213 of the control section 21 aligns the axis of the three-dimensional model, which is formed in step S1-2, in one side direction (height-wise direction) of the treatment table shown in the captured images. Then, the position adjusting unit 213 specifies feature points of the three-dimensional model. The position adjusting unit 213 also specifies feature points of the contour information related to the body surface (CT body surface shape) using the contour extraction result stored in the CT image information memory 24. In the present embodiment, the feature points of a body shape (e.g., neck, armpit) are used. The position adjusting unit 213 specifies the correspondence relationship between the feature points of the three-dimensional model and the feature points of the CT body surface shape. In this case, the position adjusting unit 213 determines the size in the height-wise direction taking account of the image intervals used in the computed tomography process and determines the arrangement of the three-dimensional model and the CT body surface shape so that the sum of distances between corresponding ones of the feature points is decreased. Here, an iterative closest point (ICP) process is used to align three-dimensional shapes of the body surfaces (sets of points defining contours of body surfaces) with each other.

The control section 21 of the treatment assist device 20 executes an output process (step S1-5). More specifically, the position adjusting unit 213 of the control section 21 replaces the body contour data, which is stored in the body contour information memory 23, with the three-dimensional model that has been aligned. Then, the position adjusting unit 213 generates combination data in which the body contour data, the CT images, and the contour extraction result (including organ and affected part) are combined and transmits the combination data to the treatment planning device 30.

Treatment Plan Assist Process

Figure 5B:
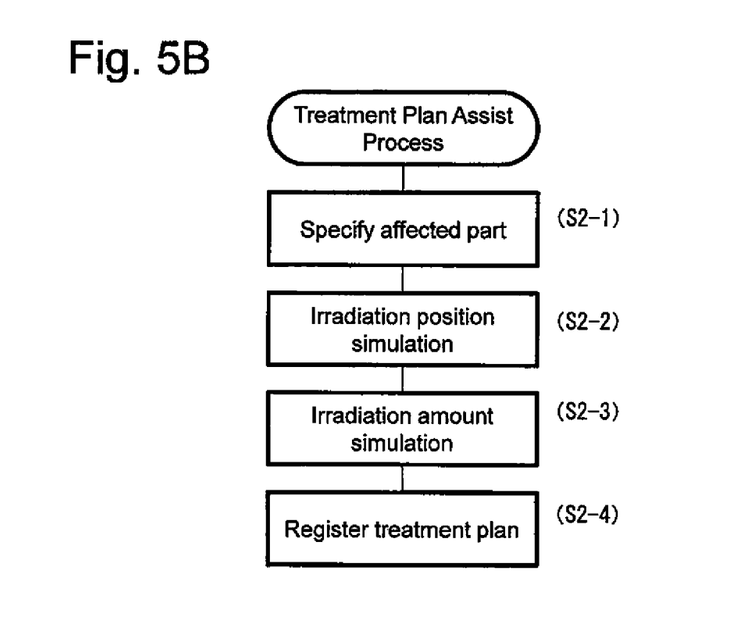
FIG. 5B is a chart showing the procedures for performing a treatment plan assist process in the system of FIG. 1.

The treatment plan assist process will now be described with reference to FIG. 5B.

The treatment planning device 30 executes a process for specifying an affected part (step S2-1). More specifically, the treatment planning device 30 outputs the combination data including the CT images to the display. The doctor checks the CT images and specifies an affected region (target) that is to be irradiated with radiation. The doctor determines the radiation quality of treatment beams emitted in the radiation treatment apparatus 15 in accordance with the type of disease of the affected part. In this case, the treatment planning device 30 obtains position information related to the affected region, which is specified in the CT images and shows the affected region in a manner distinguishable from other regions. Additionally, the doctor checks the CT images and specifies an at-risk organ, which needs to avoid the irradiation of radiation. In this case, the treatment planning device 30 obtains position information related to the at-risk organ specified in the CT images and shows the at-risk organ in a manner distinguishable from other regions.

The treatment planning device 30 executes a process for simulating an irradiation position (step S2-2). More specifically, the treatment planning device 30 searches for an irradiation position where the affected region (target) is irradiated with radiation without irradiating the at-risk organ. In this case, the irradiation position (incident direction, irradiation range) is determined taking account of the head and four limbs in the body contour information of the combination data so that the irradiation device will not come into contact with the head and four limbs.

The treatment planning device 30 executes a process for simulating an irradiation amount (step S2-3). More specifically, the treatment planning device 30 calculates the irradiation amount of radiation needed in the irradiation position for treatment. In this case, the treatment planning device 30 determines the radiation amount and the number of times irradiations are performed in accordance with the volume and depth of the affected part.

The treatment planning device 30 executes a process for registering a treatment plan (step S2-4). More specifically, the treatment planning device 30 stores the determined irradiation position and the determined irradiation amount as a treatment plan. The treatment plan is used when the treatment is performed, which will be described later.

Treatment Assist Process

Figure 6:
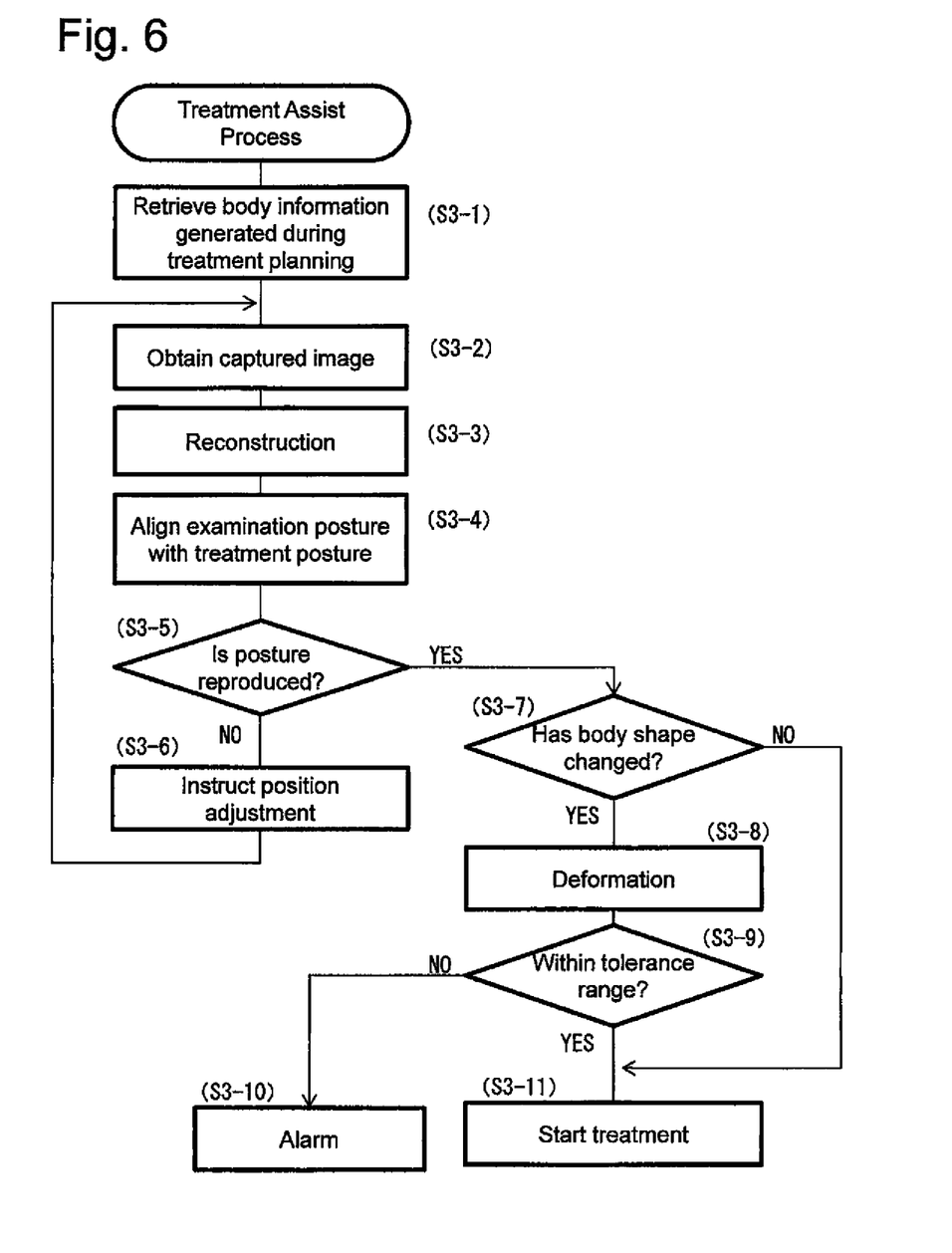
FIG. 6 is a chart showing the procedures for performing a treatment assist process in the system of FIG. 1.

The treatment assist process will now be described with reference to FIG. 6. In this case, the patient lies on the treatment table of the radiation treatment apparatus 15 in a supine position or a prone position.

The control section 21 of the treatment assist device 20 executes a process for retrieving the body information generated during the treatment planning (step S3-1). More specifically, the treatment assisting unit 214 of the control section 21 obtains the captured image associated with the patient ID and the most recent capture date and time from the three-dimensional measurement information memory 22.

The control section 21 of the treatment assist device 20 executes a process for obtaining captured images (step S3-2). More specifically, in the same manner as in step S1-1, images of the posture of the patient lying in the radiation treatment apparatus 15 (treatment posture) are captured by the 3D camera 40. At this time, the treatment assisting unit 214 of the control section 21 obtains the captured data from the 3D camera 40 together with the patient ID. The captured data includes data related to the captured images including the view point movement from a predetermined original point, the view direction, and the depth information. The treatment assisting unit 214 temporarily stores the captured data.

The control section 21 of the treatment assist device 20 executes a reconstruction process (step S3-3). More specifically, the three-dimensional measurement processing unit 211 of the control section 21 reconstructs the captured images, which are obtained from the three-dimensional measurement information memory 22, in a virtual space using the view point movement, the view direction, and the depth information to form the three-dimensional model formed during the examination. The three-dimensional measurement processing unit 211 also reconstructs the captured data, which is temporarily stored in the treatment assisting unit 214, to form the present (treatment) three-dimensional model.

The control section 21 of the treatment assist device 20 executes a process for aligning the posture formed during the examination with the posture formed during the treatment (step S3-4). More specifically, the treatment assisting unit 214 of the control section 21 performs matching on the present three-dimensional model and the three-dimensional model formed during the examination. In this case, the ICP process is also used.

The control section 21 of the treatment assist device 20 executes a process for determining whether the posture is reproduced (step S3-5). More specifically, the treatment assisting unit 214 of the control section 21 calculates the difference between the present three-dimensional model and the three-dimensional model formed during the examination. When the misalignment amount of the feature points (head, four limbs, neck, etc.) of the three-dimensional models is less than or equal to a reference value, it is determined that the posture is reproduced.

When the misalignment amount exceeds the reference value and determines that the posture is not reproduced ("NO" in step S3-5), the control section 21 of the treatment assist device 20 executes a posture adjustment instruction process (step S3-6). More specifically, the treatment assisting unit 214 of the control section 21 outputs an instruction for changing the posture of the patient on the display. In this case, the treatment assisting unit 214 outputs the present three-dimensional model and the three-dimensional model formed during the examination that are superimposed one on the other. The doctor gives an instruction to correct the posture of the patient taking account of the misalignment of the body contour data. Then, the process is restarted from the process for obtaining captured images (step S3-2).

When it is determined that the posture is reproduced ("YES" in step S3-5), the control section 21 of the treatment assist device 20 executes a process for determining whether the body shape has changed (step S3-7). More specifically, if the misalignment of the body contour data exceeds the reference value even though the positions of the feature points of the three-dimensional models indicate the same posture, the treatment assisting unit 214 of the control section 21 determines that the body shape has changed.

When it is determined that the body shape has changed ("YES" in step S3-7), the control section 21 of the treatment assist device 20 executes a deformation process (step S3-8). More specifically, the treatment assisting unit 214 of the control section 21 calculates a deformation amount that is needed to fit the three-dimensional model formed during the examination to the present three-dimensional model.

The control section 21 of the treatment assist device 20 executes a process for determining whether the body shape change is within a tolerance range (step S3-9). More specifically, the treatment assisting unit 214 of the control section 21 compares the deformation amount with a deformation reference value. When the deformation amount is less than or equal to the deformation reference value, it is determined that the body shape change is within the tolerance range.

When it is determined that the body shape change is out of the tolerance range ("NO" in step S3-9), the control section 21 of the treatment assist device 20 executes an alarm process (step S3-10). More specifically, the treatment assisting unit 214 of the control section 21 outputs an alarm to the display to prompt the doctor as the operator to recapture CT images. The doctor recaptures CT images with the 3D camera 40 in response to the alarm.

When it is determined that the body shape has not changed ("NO" in step S3-7) and when it is determined that the body shape change is within the tolerance range ("YES" in step S3-9), the control section 21 of the treatment assist device 20 executes a process for starting a treatment (step S3-11). More specifically, the treatment assisting unit 214 of the control section 21 obtains the treatment plan from the treatment planning device 30 and provides the treatment plan for the radiation treatment apparatus 15. In this case, the radiation treatment apparatus 15 performs a radiation irradiation in accordance with the treatment plan.

The treatment assist system of the present embodiment has the advantages described below.

(1) In the examination assist process of the present embodiment, the control section 21 of the treatment assist device 20 executes the process for obtaining captured images (step S1-1) and the reconstruction process (step S1-2). The control section 21 of the treatment assist device 20 also executes the process for obtaining CT images (step S1-3). Then, the control section 21 of the treatment assist device 20 executes the alignment process (step S1-4) and the output process (step S1-5). This generates the combination data in which the body contour data of the body shape of the patient is combined with the CT images. In general, only the vicinity of the affected region is captured in CT images. Thus, the entire body of the patient cannot be recognized. The combination data allows for the recognition of the entire shape of the patient and also the affected region in the entire shape.

In this case, the alignment process (step S1-4) specifies the correspondence relationship between the feature points of the three-dimensional model and the feature points of the CT body surface shape. The three-dimensional model has a lot of information related to the body surface. Thus, the alignment is accurately performed.

(2) In the treatment plan assist process of the present embodiment, the treatment planning device 30 executes the process for specifying an affected part (step S2-1), the process for simulating an irradiation position (step S2-2), and the process for simulating an irradiation amount (step S2-3). Thus, the treatment plan may be made taking account of the body shape of the patient. For example, the treatment plan may be made so that the irradiation is performed from a position that subtly affects the human body (position appropriate for treatment) where the irradiation device (gantry) will not come into contact with the body surface of the patient.

(3) In the treatment assist process of the present embodiment, the control section 21 of the treatment assist device 20 executes the process for retrieving the body information generated during the treatment planning (step S3-1), the process for obtaining captured images (step S3-2), and the reconstruction process (step S3-3). Then, the control section 21 of the treatment assist device 20 executes the process for aligning the posture formed during the examination with the posture formed during the treatment (step S3-4). The control section 21 of the treatment assist device 20 executes the process for determining whether the posture is reproduced (step S3-5). Therefore, after confirming that the posture formed during the treatment planning is reproduced, the treatment may be performed based on the treatment plan.

(4) In the treatment assist process of the present embodiment, the control section 21 of the treatment assist device 20 executes the process for determining whether the body shape has changed (step S3-7). When it is determined that the body shape has changed ("YES" in step S3-7), the control section 21 of the treatment assist device 20 executes the deformation process (step S3-8). Thus, the change in the body shape is taken into account.

Additionally, the control section 21 of the treatment assist device 20 executes the process for determining whether the body shape change is within the tolerance range (step S3-9). When it is determined that the body shape change is out of the tolerance range ("NO" in step S3-9), the control section 21 of the treatment assist device 20 executes the alarm process (step S3-10). Thus, the validity of the treatment plan may be determined when the body shape has been significantly changed.

The above embodiment may be modified as follows.

In the above embodiment, the treatment assist device 20 and the treatment planning device 30 assist in the treatment planning and the treatment. However, the hardware configuration is not limited to that of the embodiment. For example, the treatment assist device 20 may have the function of the treatment planning device 30 (treatment planning unit). In this case, the control section 21 of the treatment assist device 20 may be configured to execute the treatment plan assist process as the treatment planning unit.

In the above embodiment, the 3D camera 40 is used as a three-dimensional measurement unit that obtains three-dimensional body data. Instead, for example, a 3D scanner may be used.

In the above embodiment, the control section 21 of the treatment assist device 20 executes the alignment process (step S1-4). More specifically, the feature points of the body shape are used. However, the alignment means is not limited to that of the embodiment. For example, when performing a CT scan, a predetermined position in an image capture range of the patient (coordinates representing position of tomographic image) is irradiated with reference light (e.g., laser beam). Then, a captured image of the part of the patient including the position irradiated with the reference light is used. The position irradiated with the reference light allows for the alignment of the body contour data with the CT image.

In the above embodiment, the control section 21 of the treatment assist device 20 executes the process for determining whether the posture is reproduced (step S3-5). Additionally, when it is determined that the posture is reproduced ("YES" in step S3-5), the control section 21 of the treatment assist device 20 executes the process for determining whether the body shape has changed (step S3-7). At this time, the patient may be identified based on the body contour data. For example, a relative positional relationship of multiple feature points may be used to identify the patient. When the relative positional relationship differs between the examination and the treatment, an alarm is output.

In the above embodiment, in the treatment assist process, the control section 21 of the treatment assist device 20 executes the reconstruction process (step S3-3) and the process for aligning the posture formed during the examination with the posture formed during the treatment (step S3-4). The three-dimensional model formed during the examination is compared with the three-dimensional model formed based on images captured during the treatment. However, the posture alignment is not limited to the case of three-dimensional models (mesh models). For example, contour data and a mesh model may be used to perform the alignment. Alternatively, the three-dimensional model formed during the examination may be stored in the body contour information memory 23 and retrieved when the treatment is performed.

In the above embodiment, in the examination assist process, the control section 21 of the treatment assist device 20 executes the alignment process (step S1-4). In this case, the correspondence relationship between the feature points of the three-dimensional model and the feature points of the CT body surface shape is specified. At this time, the body contour data, which is stored in the body contour information memory 23, may be used to perform the alignment. In this case, feature points of contours of tomographies may be focused on to perform an efficient alignment.

The invention claimed is:

1. A system that assists in treatment, the system comprising circuitry configured to
   generate three-dimensional body data which is a three-dimensional model related to a body shape of a patient using data obtained from a three-dimensional measurement unit that captures a body surface of a body of the patient,
   obtain a tomographic image of the patient from a body tomographic measurement apparatus and extract a contour on the obtained tomographic image,
   execute an examination assist process, which generates body contour data in a format that is the same as the tomographic image based on the three-dimensional body data, aligns the body contour data with the contour of the tomographic image, and generates combination data in which the body contour data is combined with the tomographic image,
   execute a treatment plan assist process, which makes a treatment plan using the combination data, wherein the treatment plan specifies operation of a treatment apparatus to an affected region included in the tomographic image with a body position of a posture of the patient when treatment is performed, and
   execute a treatment assist process, which outputs a treatment instruction on the posture of the patient and the operation of the treatment apparatus that are specified in the treatment plan.

2. The system according to claim 1, wherein in the treatment assist process, the circuitry is configured to
   reobtain three-dimensional body data of the patient,
   compare the reobtained three-dimensional body data with three-dimensional body data of the posture specified in the treatment plan, and
   output a treatment instruction including a result of the comparison.

3. The system according to claim 1, wherein in the examination assist process, the circuitry is configured to align the three-dimensional body data with the tomographic image based on a feature point included in the three-dimensional body data and a feature point included in the tomographic image.

4. The system according to claim 1, wherein
   when capturing a tomographic image, the body tomographic measurement apparatus is configured to irradiate the patient with reference light that specifies a coordinate of the tomographic image,
   when generating three-dimensional body data, the three-dimensional measurement unit is configured to capture an image of the patient including a position irradiated with the reference light, and
   the circuitry is configured to align the three-dimensional body data with the tomographic image based on the position irradiated with the reference light.

5. The system according to claim 2, wherein the circuitry is configured to prompt an operator to recapture a tomographic image based on the result of the comparison.

6. A method for assisting in treatment, the method comprising:
   generating three-dimensional body data which is a three-dimensional model related to a body shape of a patient using data that is obtained from a three-dimensional measurement unit that captures a body surface of a body of the patient, obtaining a tomographic image of the patient from a body tomographic measurement apparatus and extracting a contour on the obtained tomographic image, generating body contour data in a format that is the same as the tomographic image based on the three-dimensional body data, aligning the body contour data with the contour of the tomographic image, and generating combination data in which the body contour data is combined with the tomographic image, making a treatment plan using the combination data, wherein the treatment plan specifies operation of a treatment apparatus to an affected region included in the tomographic image with a body position of a posture of the patient when treatment is performed, and outputting a treatment instruction on the posture of the patient and the operation of the treatment apparatus that are specified in the treatment plan.

7. A non-transitory computer readable storage medium comprising a program that assists in treatment with a treatment assist system, wherein the program instructs the treatment assist system to execute generating three-dimensional body data which is a three-dimensional model related to a body shape of a patient using data obtained from a three-dimensional measurement unit that captures a body surface of a body of the patient, obtaining a tomographic image of the patient from a body tomographic measurement apparatus and extracting a contour on the obtained tomographic image, generating body contour data in a format that is the same as the tomographic image based on the three-dimensional body data, aligning the body contour data with the contour of the tomographic image, and generating combination data in which the body contour data is combined with the tomographic image, making a treatment plan using the combination data, wherein the treatment plan specifies operation of a treatment apparatus to an affected region included in the tomographic image with a body position of a posture of the patient when treatment is performed, and outputting a treatment instruction on the posture of the patient and the operation of the treatment apparatus that are specified in the treatment plan.

* * * * *